United States Patent [19]

Kaschig

[11] Patent Number: 4,904,790
[45] Date of Patent: Feb. 27, 1990

[54] OPTICALLY ACTIVE STYRENE COMPOUNDS SUBSTITUTED BY A PYRIDINYL GROUP

[75] Inventor: Jürgen Kaschig, Freiburg, Fed. Rep. of Germany

[73] Assignee: Ciba-Geigy Corporation, Ardsley, N.Y.

[21] Appl. No.: 258,369

[22] Filed: Oct. 17, 1988

Related U.S. Application Data

[62] Division of Ser. No. 47,099, May 8, 1987, Pat. No. 4,800,224.

[30] Foreign Application Priority Data

May 16, 1986 [CH] Switzerland ............ 1985/86

[51] Int. Cl.$^4$ ............................................ C07D 213/36
[52] U.S. Cl. ................................................ 546/333
[58] Field of Search .................... 546/333; 514/357

[56] References Cited

PUBLICATIONS

Lowry et al, *An Introduction to Organic Chemistry*, 1940, p. 86.

Primary Examiner—Mary C. Lee
Assistant Examiner—Zinna Northington-Davis
Attorney, Agent, or Firm—Stephen V. O'Brien

[57] ABSTRACT

Optically active compounds of the formula I

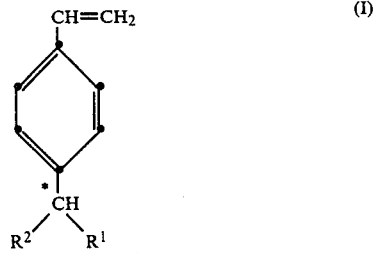

in which $R^1$ is $C_1$–$C_4$-alkyl, phenyl or benzyl, $R^2$ is a radical of the formula II or IIa

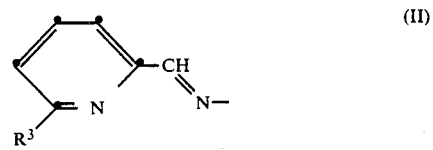

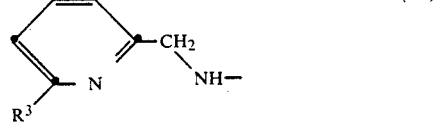

in which $R^3$ is H or —$CH_3$, or $R^1$ and $R^2$ together form a radical of the formula

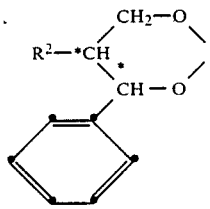

in which $R^2$ has the meaning given above; and * represents predominantly R or predominantly S configuration.

The compounds can be polymerized to give homopolymers or copolymers. The compounds and the polymers can be complexed with iridium(I) salts in the presence of a diene. The complexes are suitable as enantioselective catalysts.

2 Claims, No Drawings

OPTICALLY ACTIVE STYRENE COMPOUNDS SUBSTITUTED BY A PYRIDINYL GROUP

This is a divisional of application Ser. No. 047,099 filed on May 8, 1987, now U.S. Pat. No. 4,800,224.

The invention relates to optically active styrene derivatives having a 2-pyridinaldimino group or 2-(aminomethyl)-pyridine group, their homo- and copolymers with olefinic comonomers, complexes of the monomers and polymers with iridium(I), and their use as enantioselective catalysts for the transfer hydrogenation of prochiral ketones with secondary alcohols.

P. Hodge et al., in Polymer-supported Reactions in Organic Synthesis, John Wiley & Sons (1980), pages 281–283, describe polymer-bonded rhodium complexes of 2,3-0-isopropylidene-2,3-dihydroxy-1,4-bis(diphenylphosphinobutane) (DIOP) as enantioselective catalysts for hydrogenations.

K. Ohkubo et al. in Inorg. Nucl. Chem. Letters, Vol 17, pages 215–218 (1981), describe amberlite-bonded rhodium complexes of DIOP, which are suitable as enantioselective hydrogenation catalysts for prochiral ketones.

G. Zassinovich et al., in Journal of Organometallic Chemistry, 222, pages 323–329 (1981), describe cationic iridium(I) complexes with a 1,5-cyclooctadiene ligand and a 2-pyridinaldimine ligand which is substituted at the imine N atom by optically active α-phenylethyl or pinane-3-methyl. They act as enantioselective homogeneous catalysts in the transfer hydrogenation of prochiral ketones with isopropanol. Although high yields are achieved in the reaction, the optical yield (enantiomeric excess) is relatively low.

The invention relates to optically active compounds of the formula I

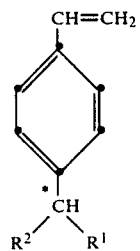  (I)

in which $R^1$ is $C_1$–$C_4$-alkyl, phenyl or benzyl, $R^2$ is a radical of the formula II or IIa

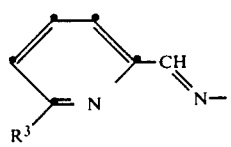  (II)

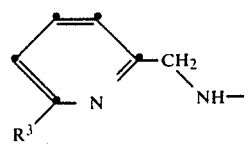  (IIa)

in which $R^3$ is H or —$CH_3$, or $R^1$ and $R^2$ together form a radical of the formula

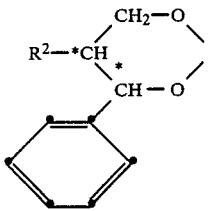

in which $R^2$ has the abovementioned meaning and * represents predominantly the R or predominantly the S configuration.

$C_1$–$C_4$-alkyl radicals $R^1$ may be branched alkyl but are preferably linear alkyl. Examples are methyl, ethyl, n-propyl, i-propyl, n-, i- and t-butyl. $R^1$ is preferably methyl or benzyl.

The compounds of the formula I are obtainable, for example, by reacting a pyridinealdehyde of the formula III

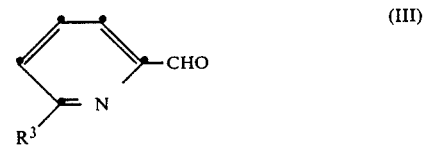  (III)

with an amine of the formula IV

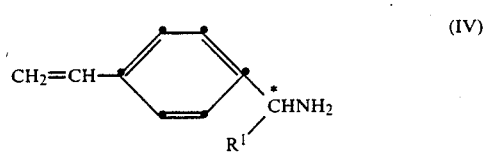  (IV)

or with an amine of the formula V

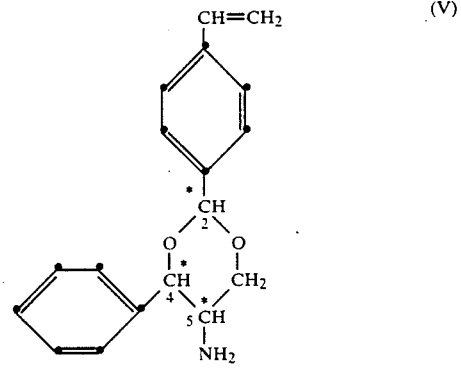  (V)

to prepare the compounds for the formula I in which $R^2$ is a radical of the formula II, and hydrogenating the resulting pyridinaldemines with $LiAlH_4$ to prepare compounds of the formula I in which $R^2$ is a radical of the formula IIa, $R^1$ and $R^3$ having the abovementioned meaning.

The reaction is advantageously carried out in a solvent and preferably at elevated temperature, in particular at 40°–120° C. Suitable solvents are, for example, hydrocarbons (for example, pentane, hexane, cyclohexane, methylcyclohexane, benzene, toluene and xylene), halohydrocarbons (for example, chloroform, methylene chloride, carbon tetrachloride and 1,1,2,2-tetrachloroethane), ethers (for example, diethyl ether, dioxane and tetrahydrofuran) and alcohols (for example, methanol, ethanol and n-propanol). Advantageously, the solvents used are those with which the resulting water of reaction can be removed from the reaction medium by azeotropic distillation. The desired compounds are advantageously isolated by distillation or crystallization. The reaction of the resulting imines of the formula I, in which $R^2$ is a radical of the formula II, with $LiAlH_4$ to prepare the amines for the formula I, in which $R^2$ is a radical of the formula IIa, is advantageously carried out in a manner known per se, at a temperature of, preferably, —20° to 30° C. in an ether (for example, diethyl ether, dioxane or tetrahydrofuran). To isolate the desired compounds, the reaction mixture is hydrolysed, and the organic phase is separated off and then chromatographed or distilled.

The pyridinealdehydes of the formula III are known and are commercially available.

The novel compounds of the formula IV in which $R^1$ is $C_1$–$C_4$-alkyl, phenyl or benzyl are obtainable by the process described in G. Wulff et al., Makromol. Chem. 183, pages 2459–2467 (1982). It has been found that the optical rotation of the (R)- and (S)-1-(4-vinylphenyl)-ethylamines stated there is too small, and consequently mixtures with an excess of one stereoisomeric amine in each case are disclosed. The values of the optical rotation for the pure stereoisomers are about 12° higher in each case. The starting materials of the formula

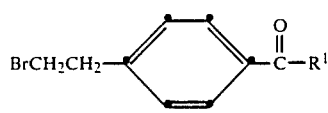

which are required for the process described by G. Wulff et al. are obtained by the process due to E. L. Foreman in JACS 62, page 1436 (1940). A traditional method of separating racemic reaction products as salts of the pure stereoisomers with optically active organic acids by fractional crystallization leads to the optically pure amines having an R or S configuration.

The novel amine of the formula V is obtained by a process analogous to the process described by K. Weinges et al. in Chem. Ber. 113, pages 710–721 (1980), by reaction of (+)-2-amino-1-phenyl-1,3-propandiolhydrobromide with p-styrylaldehyde.

The invention furthermore relates to pure stereoisomeric optically active amines of the formulae IV or V

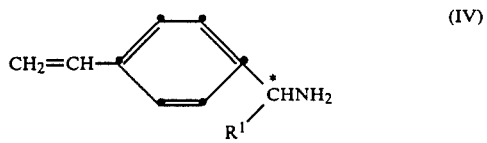

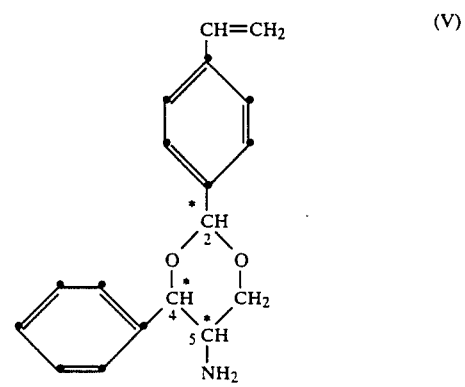

in which $R^1$ is $C_1$–$C_4$-alkyl, phenyl or benzyl and the chiral *C atom in formula IV has either the R or the S configuration, and the chiral C atoms in formula V have the 2R, 4S, 5S configuration. The compounds of the formula I are suitable as N,N-chelate ligands for the preparation of complexes.

The invention furthermore relates to iridium complexes with compounds of the formula I, wherein the complex corresponds to the formula VI or VIa

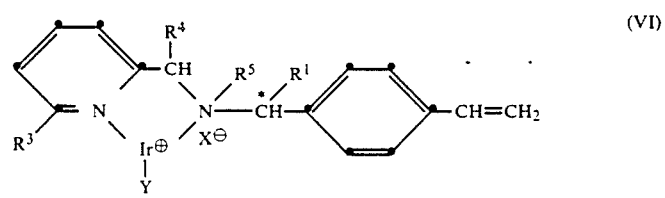

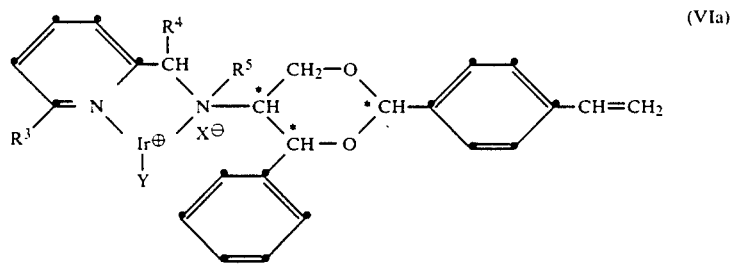

in which * represents predominantly R or predominantly S configuration, $R^1$ and $R^3$ have the meaning given above, $R^4$ and $R^5$ are each H or together form a bond, $X^-$ is an anion of a monobasic inorganic or organic acid and Y is an open-chain or cyclic diene having 6 to 10 C atoms, whose diene groups are bonded via 1 or 2 C atoms. The compounds of the formulae VI and VIa can also be in the hydrated form.

$R^1$ in formula VI is preferably methyl or benzyl.

The anion $X^\ominus$ of a monobasic inorganic or organic acid may be, for example, $F^\ominus$, $Cl^\ominus$, $Br^\ominus$, $I^\ominus$, $ClO_4^\ominus$, $NO_3^\ominus$, $BrO_3^\ominus$, $HSO_4^\ominus$, $H_2PO_3^\ominus$, $H_2PO_4^\ominus$, $BF_4^\ominus$, $B(phenyl)_4^\ominus$, $PF_6^\ominus$, $SbF_6^\ominus$, $AsF_6^\ominus$, $SbCl_6^\ominus$, $SbCl_5F^\ominus$, $HCOO^\ominus$, $CH_3COO^\ominus$, $CCl_3COO^\ominus$, $CF_3COO^\ominus$, $CH_3SO_3^\ominus$, $CCl_3SO_3^\ominus$, $CF_3SO_3^\ominus$, phenyl-$SO_3^\ominus$ or p-toluyl-$SO_3^\ominus$. In a preferred embodiment, $X^\ominus$ is halide, $BF_4^\ominus$, $ClO_4^\ominus$, $CF_3SO_3^\ominus$ or $PF_6^\ominus$.

A preferred subgroup of iridium complexes comprises those in which $X^\ominus$ in the formulae VI and VIa are $Cl^\ominus$, $Br^\ominus$, $I^\ominus$, $BF_4^\ominus$, $ClO_4^\ominus$, $CF_3SO_3^\ominus$ or $PF_6^\ominus$, and $R^4$ and $R^5$ together form a bond.

Another preferred subgroup of iridium complexes comprises those in which X—in the formulae VI and VIa are $BF_4$—, $ClO_4$—, $CF_3SO_3$— or $PF_6$— and $R^4$ and $R^5$ are each H.

Y is preferably a diene having 6 to 8 C atoms, whose diene groups are bonded, in particular, via 2 C atoms. In a preferred embodiment, Y is 1,5-cyclooctadiene, norbornadiene or 1,5-hexadiene.

Particularly preferred iridium complexes are those of the formulae

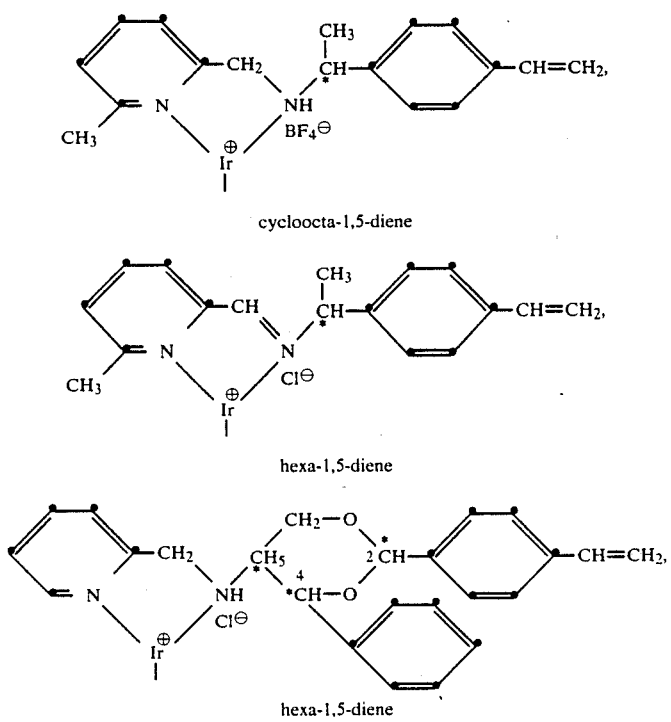

cycloocta-1,5-diene hexa-1,5-diene hexa-1,5-diene in which * represents predominantly R or predominantly S configuration or 2R, 4S, 5S configuration.

The iridium complexes of the formula VI or VIa can be obtained by processes which are known per se [cf. Inorganica Chimica Acta 73 (1983), pages 275–279], by reacting [(acetonitrile)$_2$(Y)]IrX, in which X and Y have the meaning given above, with a compound of the formula I. The preparation of the acetonitrile complex is also described there. The complexes [IrCl(Y)]$_2$ used for the preparation of the acetonitrile complex are obtainable, for example, by reacting dichlorotetrakis(alkene)-diiridium(I) (alkene: for example cyclooctene) with a diene Y. The iridium complexes of the formulae VI and VIa can also be obtained by processes which are known per se [cf. j. of Organom. Chem., 222, pages 323–329 (1981)], by reacting a diiridium complex of the formula [Ir(Y)Cl]$_2$ with a compound of the formula I.

The reactions are carried out in general at temperatures of $-10°$ to $30°$ C. in an inert solvent and in the absence of air (inert gas atmosphere). Suitable inert solvents are, for example, hydrocarbons, such as benzene, toluene, xylene, petroleum ether, hexane, cyclohexane or methylcyclohexane; and ethers, such as, for example, diethyl ether, dibutyl ether, tetrahydrofuran and dioxane, as well as halogenated hydrocarbons, for example chloroform, methylene chloride and chlorobenzene. To prepare salts of the formula VI or VIa having anions of monobasic inorganic or organic acids, the salts, in particular the chlorides, of the formula VI or VIa, can be subjected to double decomposition with an alkali metal salt $M^\oplus X'^\ominus$ either directly after the reaction or after isolation and purification and redissolution in polar solvents (for example alcohols, ethers or ketones, with or without the addition or water), and then isolated. $X'^\ominus$ is an anion of a monobasic inorganic or organic acid and differs from $X^\ominus$, and $M^\oplus$ is preferably sodium.

The compounds of the formula I are suitable for the preparation of polymers having optically active side groups. The invention furthermore relates to homopolymers and copolymers having optically active side groups, and containing, relative to the polymers, (a) 0.005 to 100 mol % of at least one repeating structural element of the formula VII

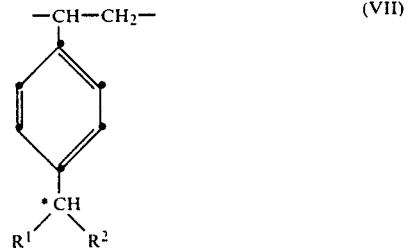

(VII)

in which $R^1$ is $C_1$–$C_4$-alkyl, phenyl or benzyl, $R^2$ is a radical of the formula II or IIa

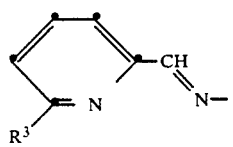

(II)

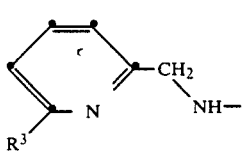

(IIa)

in which R³ is H or —CH₃, or R¹ and R² together form a radical of the formula

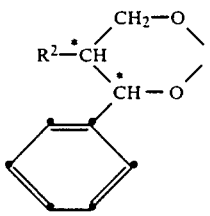

in which R² has the meaning given above; and * represents predominantly R or predominantly S configuration, and (b) 99.995 to 0 mol % of at least one structural element which is derived from an olefinic comonomer and differs from component (a).

The preferences which apply to the structural elements of the formula VII are the same as those which apply to the compounds of the formula I. The structural elements of the formula VII are preferably contained in an amount of 0.05 to 100, in particular 0.1 to 50, especially 0.1 to 10 mol %, and the structural elements of an olefinic comonomer are accordingly contained in an amount of 99.95 to 0, in particular 50 to 99.9, especially 99.9 to 90 mol %.

The structural element of the olefinic comonomer preferably corresponds to the formula VIII

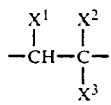

(VIII)

in which X¹ is hydrogen, X² is hydrogen, chlorine or methyl and X³ is hydrogen, methyl, chlorine, —CN or —CONR⁷R⁸, in which R⁷ and R⁸ independently of one another are H or C₁-C₁₈-alkyl, or is phenyl, methylphenyl, methoxyphenyl, cyclohexyl, —COO-alkyl having 1-12 C atoms in the alkyl moiety, —COO—phenyl, —COO—alkyl—OH having 2-6 C atoms in the alkyl moiety, —OCO—alkyl having 1-4 C atoms in the alkyl moiety, —OCO—phenyl, alkoxy having 1-20 C atoms or phenoxy, or X² is hydrogen and X¹ and X³ together form a group —CO—NR⁶—CO— or are each —COO—alkyl having 1-6 C atoms in the alkyl moiety, R⁶ being straight-chain or branched C₁-C₁₈-alkyl, cyclohexyl or phenyl which can be monosubstituted or disubstituted by C₁-C₆-alkyl, halogen, cyano, nitro and/or C₁-C₃-alkoxy.

Preferred copolymers are those in which, in formula VIII, X¹ is H, X² is H or —CH₃ and X³ is phenyl, cyclohexyl, —COO—alkyl having 1-12 C atoms in the alkyl moiety, —COO—hydroxyalkyl having 2 to 4 C atoms in the alkyl moiety or —CONR⁷R⁸, in which R⁷ and R⁸ independently of one another are H or C₁-C₁₂-alkyl.

Particularly preferred copolymers are those in which, in the formula VIII, X¹ and X² are H and X³ is phenyl, or X¹ is H, X² is —CH₃ and X³ is —COO—alkyl having 1 to 12 C atoms in the alkyl moiety.

Alkyl radicals X³, R⁶, R⁷ and R⁸ can be linear or branched and preferably contain 1 to 12, in particular 1 to 6, C atoms. The polymers according to the invention can furthermore contain up to 60 mol %, relative to the monomers present, of structural elements of an olefinically diunsaturated or polyunsaturated crosslinking agent. Suitable polyunsaturated crosslinking agents are, for example, divinylbenzenes, divinyltoluenes, divinylnaphthalenes, divinylxylenes, divinylethylbenzenes, divinyl sebacate, trivinylbenzenes, trivinylnaphthalenes and polyvinylanthracenes; ethylene glycol diacrylate, ethylene glycol dimethacrylate, N,N'-methylenediacrylamide, N,N'-methylene-dimethylacrylamide, N,N'-ethylenediacrylamide, polyvinyl ethers of ethylene glycol, propanetriol, pentaerythritol and resorcinol.

The crosslinking agent is preferably used in an amount of 0.1-10 mol %. Preferred crosslinking agents are divinylbenzenes. By a suitable choice of the comonomers and/or crosslinking agents, the properties of the polymers can be adapted to the desired specific applications.

The polymers can have a mean molecular weight ($\overline{M}_w$) of 1,000 to 5,000,000, preferably 5,000 to 1,000,000, in particular 5,000 to 500,000 (osmometric determination).

The polymers according to the invention can be obtained in a known manner, by polymerizing (a) 0.005 to 100 mol % of at least one monomer of the formula I and (b) 0 to 99.995 mol % of at least one olefinic comonomer which differs from component (a).

Free radical polymerization is preferred. About 0.01 to 5% by weight, preferably 0.01 to 1.5% by weight, relative to the total weight of the monomers and any crosslinking agents, of conventional free radical initiators, such as inorganic or organic peroxides or azo compounds, for example hydrogen peroxide, potassium peroxydisulfate, tert-butyl hydroperoxide, di-tert-butyl peroxide, peracetic acid, dibenzoyl peroxide, diacyl peroxides, cumene hydroperoxide, tert-butyl perbenzoate, tert-alkyl peroxydicarbonates and α,α'-azoisobutyronitrile, are advantageously used in the polymerization. The reaction temperatures for the free radical polymerization are in general between about 30° and 100° C. The polymerization can be carried out in the homogeneous phase, for example in the absence of a solvent or in solution, or in the heterogeneous phase, i.e. by precipitation polymerization, emulsion polymerization or suspension polymerization. Polymerization in solution is preferred. Suitable solvents are, for example, toluene, N,N-dimethylformamide, N,N-dimethylacetamide, acetonitrile, tetrahydrofuran and dioxane.

Some or all of the polymers according to the invention can be complexed with iridium(I) salts. The invention furthermore relates to polymers wherein at least some of the structural elements of the formula VII are complexed with iridium(I) and correspond to the formula IX or X

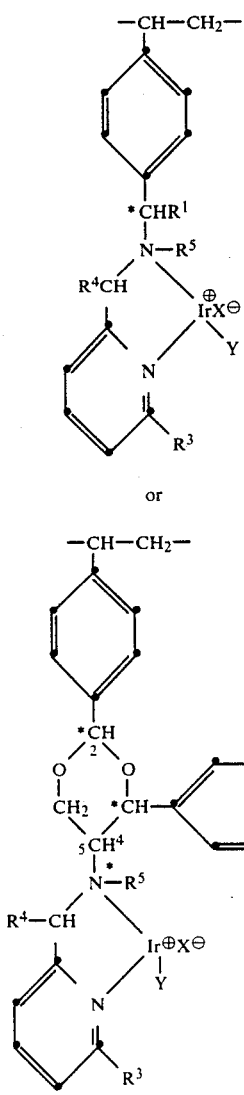

in which $R^1$ is $C_1$-$C_4$-alkyl, phenyl or benzyl, $R^3$ is H or —$CH_3$, $R^4$ and $R^5$ are each H or together form a bond, $X^\ominus$ is the anion of a monobasic inorganic or organic acid and Y is an open-chain or cyclic diene having 6 to 10 C atoms, whose diene groups are bonded via 1 or 2 C atoms. The preferences stated above apply to $R^1$ to $R^5$, $X^\ominus$ and Y and to the polymers. Preferably, at least 50, in particular at least 90, mol % of the structural elements of the formula VII which are present are complexed.

The complexed polymers can be prepared if (A) (a) 0.005 to 100 mol % of at least one monomer of the formula VI or VIa, with or without a monomer of the formula I, and (b) 0 to 99.995 mol % of at least one olefinic comonomer which differs from component (a) are polymerized, or (B) a homopolymer or copolymer according to the invention, having structural elements of the formula VII, is reacted in solution with [(acetonitrile)$_2$(Y)]IrX or with di-[μ-chlorotetrakis (cyclooctene)-diiridium-(I)]Cl and a diene Y, X being the anion of a monobasic inorganic or organic acid.

Process (A) is carried out essentially in the same way as the polymerization for the preparation of the non-complexed polymers according to the invention. Process (B) is carried out essentially in the same way as the preparation of the complexes of the formula VI or VIA.

The iridium complexes according to the invention and complexed polymers are suitable as homogeneous or heterogeneous enantioselective catalysts for the hydrogenation of unsaturated organic compounds which preferably have at least one prochiral C atom. In particular, they are suitable as catalysts for transfer hydrogenation, preferably of ketones.

The invention furthermore relates to the use of iridium complexes of the formulae VI and VIa as homogeneous enantioselective catalysts for the transfer hydrogenation of prochiral ketones with secondary alcohols, and the use of complexed polymers according to the invention as homogeneous or heterogeneous enantioselective catalysts for the transfer hydrogenation of prochiral ketones with secondary alcohols. A particularly suitable secondary alcohol is isopropanol. The reaction is advantageously carried out in the absence of oxygen and at elevated temperature (for example 50°–150° C.). The secondary alcohol used is advantageously employed as a solvent. The catalyst concentration is preferably $10^{-1}$ to $10^{-5}$ mol/l, relative to the reaction volume. The reaction is preferably carried out in the presence of a base, in particular NaOH.

The polymerizable compounds of the formula I and their polymers are valuable optically active ligands for the preparation of chiral, homogeneous and heterogeneous catalysts with various complex-forming metal compounds. Surprisingly, the monomeric metal complexes can be polymerized. A particular advantage of the heterogeneous, polymeric catalysts is that they can be readily removed from the reaction mixture and reused. As catalysts, the monomeric metal complexes have good selectivity (optical yield) and high yields, which are even surpassed by the heterogeneous polymeric catalysts. The examples below illustrate the invention in more detail.

(A) PREPARATION OF STARTING MATERIALS

Example (a):

(2R, 4S, 5S)-(+)-5-amino-2-(4-vinylphenyl)-4-phenyl-1,3-dioxane 5.9 g (0.021 mol) of phosphorus pentoxide are added at 5° C. to a stirred mixture of 6 g (0.024 mol) of (+)-2-amino-1-phenyl-1,3-propanediol hydrobromide, 25 ml of p-styrylaldehyde and a pinch of 2,6-di-tert-butyl-p-cresol. The suspension is kept at 20° C. by cooling with ice and is stirred for 6 hours. Thereafter, 20 ml of concentrated potassium carbonate solution are added at 0° C., and a layer of 50 ml of ethyl acetate is introduced on top. The mixture is stirred vigorously with the addition of 50 ml of ice water, after which the mixture is freed from the solid constituents by filtration. The aqueous phase is separated off and washed twice with ethyl acetate. The combined organic phases are washed with concentrated sodium chloride solution (brine), dried over sodium sulfate and substantially freed from the solvent under about 2 kPa.

The residue is suspended in 250 ml of methanol, and 20 ml of acetic acid, a pinch of 2,6-di-tert-butyl-p-cresol and 42.3 g of acethydrazide-trimethylammonium chloride (Girard reagent T) are added. After stirring for 15 hours at room temperature, the reaction mixture is poured onto 1.5 l of ice water. 33.3 g of sodium carbonate are added in portions, and the product is then extracted four times with about 200 ml of ethyl acetate. After the solution has been dried over sodium sulfate, it is freed from the solvent under 1.5 kPa. The yellow oil which remains is purified by chromatographing it over silica gel (mobile phase: methanol). 3.9 g (57% of theory) of an oily product are obtained.

$[\alpha]_D^{20} = +35.7°$ (c=1.143, chloroform).

250 MHz−$^1$HFT-NMR (CDCl$_3$): δ=1.55 (s; 2H), 2.95 (m; 1H), 4.31 (m; 2H), 5.13 (m; 1H), 5.27 (m; 1H), 5.72 (s; 1H), 5.76 (m; 1H), 6.74 (m; 1H), 7.24–7.61 (m; 9H)ppm.

Example b:

(R), (S)-1-[4-(2-bromoethyl)-phenyl]-2-phenylethylamine hydrochloride

A solution of 50 g (0.66 mol) of ammonium acetate in 200 ml of methanol, 2.7 g (0.43 mol) of sodium cyanoborohydride and about 100 mg of 4-tert-butylpyrocatechol are added to a solution of 20 g (0.066 mol) of 4-(2-bromoethyl)-phenyl benzyl ketone in 100 ml of dioxane. After the mixture has been stirred for 48 hours at room temperature, it is acidified with 50 ml of concentrated hydrochloric acid (pH 2). Thereafter, methanol and dioxane are substantially distilled off under about 2 kPa and are replaced by ethyl acetate. The solution is washed with twice 100 ml of water and evaporated down under about 2 kPa. The residue is taken up with ethanol/diethyl ether (1:1). The white precipitate formed is filtered off, and the filtrate is evaporated down to give an oil. After the addition of 50 ml of ethyl acetate, the product begins to crystallize. It is filtered off under suction and dried. Yield: 10.8 g (48% of theory) of white crystals. Melting point: 165°–168° C./decomposition.

Elemental analysis:
Found: C 56.49; H 5.31; N 4.29; Br 23.02%.
Calculated for C$_{16}$H$_{19}$NBrCl (340.69): C 56.44; H 5.62; N 4.11; Br 23.45%.

(R), (S)-1-(4-vinylphenyl)-2-phenylethylamine hydrochloride

A sodium alcoholate solution is prepared from 14.7 g (0.634 mol) of sodium and 480 ml of ethanol. 65 g (0.191 mol) of (R), (S)-1-[4-(2-bromoethyl)-phenyl]-2-phenylethylamine hydrochloride are added. The yellow suspension is heated under reflux for 15 minutes and, after cooling, is poured onto 1 l of ice water. The product is extracted with three times 500 ml of diethyl ether. The ether phase is dried with sodium sulfate, and hydrogen chloride gas is added. After the ether has been distilled off, the crude product is recrystallized from ethanol diethyl ether (1:1). Yield: 32.2 g (65% of theory) of white crystals.

Melting point: 268°–271° C./decomposition.
Elemental analysis:
Found: C 70.96; H 7.27; N 5.40; Cl 12.96; H$_2$O 3.78%
Calculated for C$_{16}$H$_{18}$NCl: 0.57 H$_2$O; C 71.78%; H 7.14;
N 5.19; Cl 13.13; H$_2$O 3.78%.

Bis-(S)-1-(4-vinylphenyl)-2-phenylethylamine L-tartrate

From (R), (S)-2-(4-vinylphenyl)-2-phenylethylamine hydrochloride, the free base is obtained by treatment with an ion exchanger (Amberlyst A 26, OH form, mobile phase: methanol). 23.1 g (0.103 mol) of the free base are dissolved in 500 ml of ethyl acetate, and 7.75 g (0.0502 mol) of L-(+)-tartaric acid, dissolved in 40 ml of ethanol, are added. After 48 hours at about −15° C., 25 g of a crystalline product are obtained; $[\alpha]_D^{20} = +17.7°$ (MeOH, c=0.926). This is recrystallized six times from ethanol, the optical rotation increasing to the value $[\alpha]_D^{20} = +134.5°$ (MeOH, c=1.006).

Yield: 3.8 g
Elemental analysis:
Found: C 71.50; H 6.76; N 4.97; O 16.43%;
Calculated for C$_{36}$H$_{42}$O$_6$N$_2$:
C 72.22; H 7.07; N 4.68; O 16.03%.

(S)-1-(4-vinylphenyl)-2-phenylethylamine 2.87 g (0.0048 mol) of the tartrate described above are dissolved in 50 ml of ethyl acetate. 50 ml of concentrated sodium hydroxide solution are added. The ethyl acetate phase is separated off, and the aqueous phase is further extracted with twice 25 ml of ethyl acetate. The combined organic phases are washed with 25 ml of brine and dried over sodium sulfate, a pinch of di-tert-butyl-p-cresol is added and the mixture is evaporated down under about 2 kPa. The residue is distilled at 180° C. and under 9·10$^{-3}$ Pa in a bulb tube furnace.

Yield: 2.0 g of an oil which crystallizes.
$[\alpha]_D^{20} = +30.4°$ (chloroform, c=1.466).
Elemental analysis:
Found: C 85.66, H 7.66; N 6.16%.
Calculated for C$_{16}$H$_{17}$N:
C 86.06; H 7.68; N 6.28%.

Example c:

(R)-1-(4-vinylphenyl)-ethylamine L-malate 37.4 g (0.279 mol) of L-(−)-malic acid are added to a solution of 41.06 g (0.279 mol) of (R), (S)-1-(4-vinylphenyl)-ethylamine in 250 ml of methanol at 0° C. After 15 hours, the precipitated crystals (31.0 g) are filtered off under suction, and the mother liquor is evaporated down in vacuo until crystallization begins again. A further 15 g of product are obtained. The crystal fractions are combined and recrystallized twice, in each case from 250 ml of methanol, with the addition of about 50 mg of di-tert-butyl-p-cresol.

Yield: 15.2 g of white crystalline powder.
$[\alpha]_D^{20} = +2.10°$ (H$_2$O, c=0.95).

(R)-1-(4-vinylphenyl)-ethylamine 14.0 g of the crystalline powder [(R)-1-(4-vinylphenyl)-ethylamine L-malate] are dissolved in a little water, and a layer of 100 ml of ethyl acetate is introduced on top. The mixture is rendered alkaline (pH>10) with 30% sodium hydroxide solution, and the ethyl acetate phase is separated off. The aqueous phase is rinsed with twice 50 ml of ethyl acetate. The organic phases are combined, washed with concentrated sodium chloride solution (brine), dried over sodium sulfate and evaporated down, with the addition of a pinch of di-tert-butyl-p-cresol. The residue is distilled under a high vacuum. Boiling point: 54° C./1·10$^{-2}$ Pa, yield: 7.4 g of colorless liquid.

$[\alpha]_D^{20} = +36.2°$ (chloroform, c=0.968).

Example d:

(S)-1-(4-vinylphenyl)-ethylamine D-malate

The mother liquors obtained in the crystallizations described under Example c are combined, and substantially freed from the solvent under about 2 kPa. Using a method analogous to that described in Example c, the amine is liberated and distilled. Similarly to Example c, the amine (18.8 g) is dissolved in 125 ml of methanol and reacted with D-(+)-malic acid (17.12 g). The crystals obtained are recrystallized twice from methanol.

Yield: 15.0 g of white crystalline powder.

$[\alpha]_D^{20} = 1.84°$ (H$_2$O, c = 1.25).

(S)-1-(4-vinylphenyl)-ethylamine

Analogously to Example c, 14 g of (S)-1-(4-vinylphenyl)-ethylamine L-malate are treated with sodium hydroxide. After the mixture has been worked up, 7.5 g of a colorless liquid are obtained. Boiling point: 53° C./1·10$^{-2}$ Pa, $[\alpha]_D^{20} = -34.9°$ (chloroform, c = 0.986).

EXAMPLE 1:

N-(6-methyl-pyridine-2-carbaldehyde)-(R)-1-(4-vinylphenyl)-ethylimine

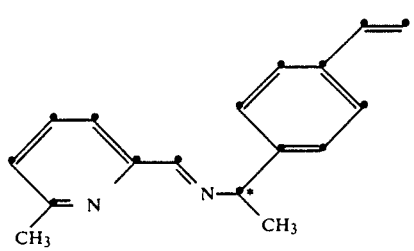

A solution of 1.69 g (13.9 mmol) of 6-methylpyridine-2-carbaldehyde, 2.05 g (13.9 mmol) of (R)-1-(4-vinylphenyl)-ethylamine and 25 ml of ethanol is heated under reflux for 1 hour. The solvent is then distilled off under about 3 kPa, and the residue is distilled in a bulb tube furnace at 170° C. and under 0.11 Pa. 3.3 g (88% of theory) of an oil are obtained, which crystallises at room temperature. Melting point: about 25° C.

$[\alpha]_D^{20} = 21.6°$ (c = 1.036, chloroform).

Elemental analysis:

Found: C 81.71; H 7.25; N 11.02%.

Calculated for C$_{17}$H$_{18}$N$_2$ (250.35):

C 81.56; H 7.25; N 11.19%.

EXAMPLE 2:

N-(6-methylpyridine-2-carbaldehyde)-(S)-1-(4-vinylphenyl)-2-phenyl-ethylimine

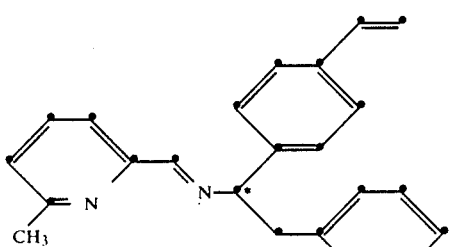

A solution of 0.54 g (4.5 mmol) of 6-methyl-pyridine-2-carbaldehyde, 1.0 g (4.5 mmol) of (S)-1-(4-vinylphenyl)-2-phenyl-ethylamine and 10 ml of benzene is evaporated down at room temperature and under about 3 kPa. A further 10 ml of benzene are added in order to distill off residual water of reaction together with benzene under about 3 kPa. The process is repeated twice more.

After the solvent has been completely removed under about 1.5 Pa, 1.5 g (97% of theory) of white crystals are obtained.

Elemental analysis:

Found: C 84.55; H 6.74; N 8.32%.

Calculated for C$_{23}$H$_{22}$N$_2$ (326.45): C 84.62; H 6.79; N 8.58%

EXAMPLE 3:

N-(Pyridine-2-carbaldehyde)-(2R,4S,5S)-5-imino-2-(4-vinylphenyl)-4-phenyl-1,3-dioxane

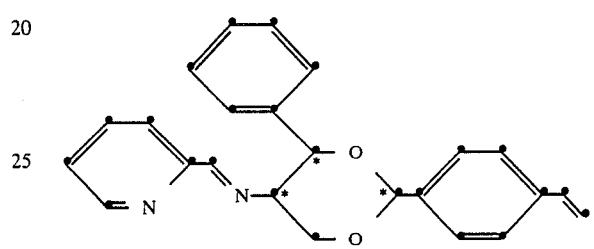

A solution of 1.60 g (15.0 mmol) of pyridine-2-carbaldehyde, 4.25 g (15.1 mmol) of (2R,4S,5S)-5-amino-2-(4-vinylphenyl)-4-phenyl-1,3-dioxane in 50 ml of benzene is evaporated down at 40° C. and under about 3.5 Pa. A further 50 ml of benzene are added in order to distill off residual water of reaction together with benzene in vacuo. The residue is taken up with 20 ml of benzene and freed from solid constituents by filtration, and petroleum ether is added. During this process the product crystallizes. It is filtered off under suction and dried at 20° C./1 Pa. Crude yield: 3.8 g of a beige powder (66% of theory). 2.3 g of white crystals are obtained after crystallization from 15 ml of ethanol. Melting point 113°-114° C., $[\alpha]_D^{20} = +196.0°$ (c = 1.108, chloroform)

Elemental analysis:

Found : C 77.10; H 6.13; N 7.20; O 9.09%.

Calculated for C$_{24}$H$_{22}$N$_2$O$_2$ (370.45):

C 77.81; H 5.99; N 7.56; O 8.64%.

EXAMPLE 4:

2-{N-[(R)-1-(4-vinylphenyl)-ethyl]-aminomethyl}-6-methylpyridine

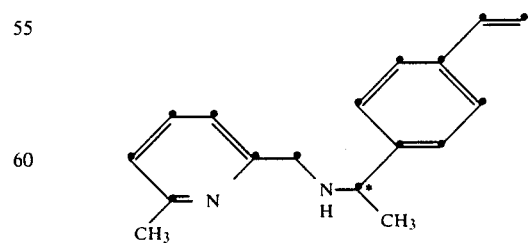

A solution of 1 g of N-(6-methyl-pyridine-2-carbaldehyde)-(R)-1-(4-vinylphenyl)-ethylimine (Example 1) and 5 ml of dry tetrahydrofuran is added dropwise to a mixture of 5 ml of dry tetrahydrofuran and 0.42 g of lithium alanate at 0° C. and in the absence of moisture. The mixture is then stirred for 4 hours without cooling, after which it is hydrolysed at 0° C. with 1 ml of concentrated sodium sulfate solution. The precipitate is filtered off and washed with ethyl acetate. The aqueous phase of the filtrate is separated off and rinsed with ethyl acetate, and the combined organic phases are dried over sodium sulfate. After the solvent has been evaporated off at room temperature and under about 1.5 Pa, the residue is distilled in a bulb tube furnace at a furnace temperature of 250° C. and under 0.01 Pa. 0.63 g (63% of theory) of a yellow oil is obtained.

$[\alpha]_D^{20} = +52.9$ (0.926, chloroform).

250 MHz—$^1$HFT-NMR (CDCl$_3$):

$\delta = 1.41$ (d; 3H), 2.26 (broad; 1H), 2.53 (s; 3H), 3.70 (s; 2H), 3.82 (q; 1H), 5.21 (m; 1H), 5.72 (m; 1H), 6.71 (m; 1H), 6.97–7.50 (m; 7H)ppm.

EXAMPLE 5:

2-{[N-[(S)-1-(4-vinylphenyl)-2-phenyl-ethyl]-aminomethyl}-6-methyl-pyridine

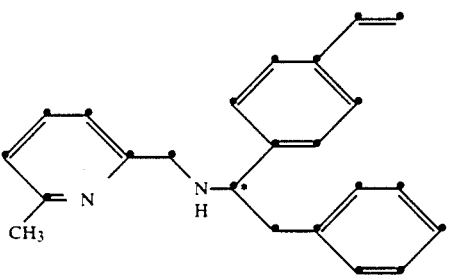

1.15 g of N-(6-methyl-pyridine-2-carbaldehyde)-(S)-1-(4-vinylphenyl)-2-phenyl-ethylimine are reduced with 0.2 g of lithium alanate similarly to Example 4. 0.9 g (83% of theory) of a colorless oil is obtained, which is chromatographed over silica gel (mobile phase: ethyl acetate). After the second fraction (main fraction) has been evaporated down and the remaining oil dried in vacuo (about 1.2 Pa), 0.6 g of product is obtained as a colorless oil.

$[\alpha]_D^{20} = -15.4°$ (c = 1.414, chloroform).

Elemental analysis:

Found: C 84.21 H 7.20 N 9.03%.

Calculated for C$_{23}$H$_{24}$N$_2$ (328.46):

C 84.11; H 7.37; N 8.53%.

EXAMPLE 6:

2-{N-[(2R,4S,5S)-2-(4-vinylphenyl)-4-phenyl-1,3-dioxan-5-yl]-aminomethyl}-pyridine

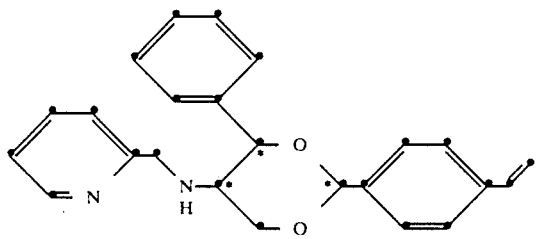

1.0 g of N-(pyridine-2-carbaldehyde)-(2R,4S,5S)-5-imino-2-(4vinylphenyl)-4-phenyl-1,3-dioxane (Example 3) is reduced with 0.16 g of lithium alanate similarly to Example 4. After chromatography over silica gel (mobile phase: ethyl acetate), 0.55 g of a yellowish oil is obtained.

$[\alpha]_D^{20} = +58.1$ (c = 1.080, chloroform).

250 MHz—$^1$HFT-NMR (CDCl$_3$):

$\delta = 2.28$ (broad; 1H), 2.71 (d; 1H), 3.68–3.93 (m; 2H), 4.10–4.49 (m; 2H), 5.12 (d; 1H), 5.26 (m; 1H), 5.74 (s; 1H), 5.77 (m; 1H), 6.72 (m; 1H), 6.76–8.35 (m; 13H).

EXAMPLE 7:

[Ir(N,N)(HD)Cl],N,N: Compound according to Example 1

Under argon protective gas, 0.600 g (0.68 mmol) of di-μ-chlorotetrakis(cyclooctene)diiridium(I) is dissolved in 50 ml of benzene. 4.4 ml of 1,5-hexadiene (HD) are added at 10° C. The mixture is stirred for 30 minutes at room temperature, after which 375 mg (1.5 mmol) of N-(6-methylpyridine-2-carbaldehyde)-(R)-1-(4-vinylphenyl)-ethylimine (Example 1) are added.

After the mixture has been stirred for 1 hour at room temperature, 100 ml of n-hexane are added in the absence of air. The product crystallizes out in the course of 2 hours at 0° C. Under an argon atmosphere, it is filtered off under suction, washed with n-hexane and dried for 3 hours under 1.3 Pa. Yield: 0.500 g (66% of theory) of a beige powder.

Elemental analysis:

Found: C 48.05; H 5.16; N 4.99; Ir 34.3%.

Calculated for C$_{23}$H$_{28}$N$_2$IrCl (560.16):

C 49.32; H 5.04; N 5.00; Ir 34.31%.

EXAMPLE 8:

[Ir(N,N)(HD)I], N,N: Compound according to Example 3

0.492 g (0.55 mmol) of di-μ-chlorotetrakis(cyclooctene) diiridium(I) is dissolved in 80 ml of acetone under argon protective gas. 3.4 ml of 1,5-hexadiene (HD) are added at 5° C. The mixture is heated to 35° C. for 10 minutes, after which a solution of 0.380 g (2.5 mmol) of sodium iodide in 12 ml of water is added at 0° C. in the absence of air, followed immediately by a solution of N-(pyridine-2-carbaldehyde)-(2R,4S,5S)-5-imino-2-(4-vinylphenyl)-4-phenyl-1,3-dioxane (Example 3) in 4 ml of acetone. After 1 hour, the mixture is evaporated down to half its volume. In the course of one hour, the product crystallizes out at O° C. It is filtered off under suction under protective gas, washed with about 40 ml of water and dried over phosphorus pentoxide for 8 hours under 0.13 Pa. Yield: 0.520 g (67% of theory) of dark blue crystals.

Elemental analysis:

Found: C 46.59; H 4.16; N 3.60; I 16.31;

Calculated for C$_{30}$H$_{32}$N$_2$O$_2$Ir (771.71); C 46.69; H 4.18, N 3.63; I 16.44%.

EXAMPLE 9:

[Ir(N,N)(COD)]BF$_4$, N,N: compound according to Example 4, COD: cycloocta-1,5-diene 0.469 g (1.0 mmol) of [bis(acetonitrile)cycloocta-1,5-diene]iridium tetrafluoborate is dissolved in 15 ml of dichloromethane under argon protective gas. A solution of 5 ml of dichloromethane and 0.252 g (1.0 mmol) of 2-{N-[(R)-1-(4-vinylphenyl)-ethyl]-aminomethyl}-6-methyl-pyridine (Example 4) is added dropwise at room temperature and while stirring. After 1 hour, the mixture is evaporated down under about 600 Pa to about one third of its volume. 60 ml of diethyl ether are added, the product separating out as a solid precipitate in the course of 2 hours. The product is filtered off under suction under an argon atmosphere, washed three times with diethyl ether and dried for 15 hours under 0.1 Pa. Yield: 0.588 g (92% of theory) of ochre yellow crystals.

Elemental analysis:
Found: C 45.07; H 5.12; N 4.27; Ir 28.5%.
Calculated for $C_{25}H_{32}N_2IrBF_4$: 1.5 $H_2O$ (666.57):
C 45.05; H 5.29; N 4.20; Ir 28.83%.

EXAMPLE 10:

[Ir(N,N)(COD)]BF$_4$,N,N: Compound according to Example 5

0.469 g (1.0 mmol) of [bis(acetonitrile)cycloocta-1,5-diene]iridium tetrafluoborate is reacted with 0.316 g (1.0 mmol) of 2-{N-[(S)-1-(4-vinylphenyl)-2-phenyl-ethyl]-aminomethyl}-6-methylpyridine (Example 5) analogously to Example 9. After working up in a corresponding manner, 0.641 g (91% of theory) of yellow crystals are obtained.

Elemental analysis:
Found: C 49.80; H 5.19; N 3.82; Ir 24.9%; F 10.32%.
Calculated for $C_{31}H_{36}N_2IrBF_4$·2 $H_2O$ (751.68):
C 49.53; H 5.36; N 3.79; Ir 25.57%; F 10.11%.

EXAMPLE 11:

[Ir(N,N)(COD)BF$_4$,N,N: Compound according to Example 6

0.260 g (0.605 mmol) of [bis(acetonitrile)cycloocta-1,5-diene]iridium tetrafluoborate is reacted with 0.225 g (0.605 mmol) of 2-{N-[(2R,4S,5S)-2-(4-vinylphenyl)-4-phenyl-1,3-dioxan-5-yl]aminomethyl}-pyridine (Example 6) analogously to Example 9. After working up in a corresponding manner, 0.380 g (79% of theory) of orange brown crystals are obtained.

Elemental analysis:
Found: C 48.36; H 4.93; N 3.74; F 10.18; Ir 24.5%.
Calculated for $C_{32}H_{40}N_2O_4IrBF_4$·2 $H_2O$ (795.69):
C 48.30; H 5.07; N 3.52; F 9.55; Ir 24.16%.

EXAMPLE 12:

Copolymer of [Ir(N,N)(HD)Cl] according to Example 7 (2 mol %), 2-ethylhexyl methacrylate (96 mol %) and technical-grade divinylbenzene (2 mol %)

30.0 mg (0.0536 mmol) of the complex, prepared according to Example 7, 6.97 mg (0.0536 mmol) of technicalgrade divinylbenzene (techn. DVB) and 509.8 mg (2.571 mmol) of freshly distilled 2-ethylhexyl methacrylate are dissolved in 7 ml of tetrahydrofuran. The dark reddish brown solution is mixed with 3.3 mg of azobisisobutyronitrile (AIBN), dissolved in 1 ml of tetrahydrofuran, in an ampoule flushed with argon. The mixture is heated to 70° C. in the absence of air, and the same amount of AIBN is added after 24 hours and then after a further 18 hours. After polymerization has continued for a further 30 hours at 75° C., a finely divided emulsion which is fluorescent red in transmitted light is obtained. The residual content of 2-ethylhexyl methacrylate monomer is determined by means of gas chromatography (CW-20 M) as 7 % of the amount originally used.

The volume is evaporated down to 3.5 ml, and the emulsion is used for catalysis. The catalyst capacity is determined as $1.148 \cdot 10^{-5}$ mol of repeating units of iridium complex per 1 ml of emulsion.

EXAMPLE 13:

Copolymer of N,N-ligand (according to Example 1, 5 mol %) and styrene (95 mol %)

0.2504 g (1 mmol) of N-(6-methyl-pyridine-2-carbaldehyde)-(R)-1-vinylphenyl)-ethylimine (N,N-ligand) and 1.979 g (19.0 mmol) of freshly distilled styrene are dissolved in 5 ml of benzene. In an ampoule flushed with argon, the solution is mixed with 24.6 mg of AIBN and heated for 20 hours at 70° C. The viscous solution formed is diluted with about ⅓ of its volume of benzene. By pouring the mixture into 250 ml of methanol, a white powder is obtained. It is dissolved in tetrahydrofuran and reprecipitated from methanol. It is separated off from the supernatant precipitating agent by centrifuging, and dried for 15 hours at 40° C. and under 0.12 Pa. Yield: 1.03 g, $[\alpha]_D^{23} = +0.44°$ (c=4.966, chloroform).

Elemental analysis:
Found: C 90.43; H 7.70; N 1.39%,
Calculated for 0.056 ($C_{17}H_{18}N_2$)+0.944 ($C_8H_8$):
C 90.92; H 7.68; N 1.40%.
Ligand capacity: 0.499 mmol/g.

EXAMPLE 14:

Copolymer of [Ir(N,N)(HD)Cl] (5 mol %) and styrene (95 mol %) by polymer-analogous reaction at the polymer ligand according to Example 13

0.0893 g of di-μ-chlorotetrakis(cyclooctene)diiridium(I) BF$_4$ is dissolved in 5 ml of benzene under argon protective gas. 1.2 ml of 1,5-hexadiene (HD) are added at 10° C. The mixture is stirred for 30 minutes at room temperature, after which a solution of 0.4000 g of polymer, prepared according to Example 13, and 5 ml of benzene is added dropwise. A dark red solution is formed, which, after it has been stirred for 1 hour in the absence of air, is evaporated down to about ⅓ of its volume and used directly for the catalytic transfer hydrogenation. The catalyst capacity is determined as $1.766 \cdot 10^{-5}$ mol of repeating units per 1 ml of solution.

EXAMPLE 15:

Copolymer of [Ir(N,N(COD)BF$_4$ (according to Example 9) (2 mol %), 2-ethylhexyl methacrylate (96 mol %) and 1,4-divinylbenzene (2 mol %)

95.9 mg (0.15 mmol) of the complex, prepared according to Example 9, 19.5 mg (0.15 mmol) of 1,4-divinylbenzene (1.4-DVB) and 1.428 g (7.2 mmol) of freshly distilled 2-ethylhexyl methacrylate are dissolved in 12 ml of tetrahydrofuran. The ochre solution is mixed with 9.23 mg of AIBN, dissolved in 0.2 ml of tetrahydrofuran, in an ampoule flushed with argon. The mixture is heated to 70° C., in the absence of air, and the same amount of AIBN is added again after 65 hours. After a further 48 hours at 70° C., a viscous, finely divided emulsion having a pale reddish brown color is obtained. The volume is brought to 10 ml, and the catalyst capacity is determined as $1.42 \cdot 10^{-5}$ mol of repeating units of iridium complex per 1 ml of emulsion.

EXAMPLE 16:

Copolymer of [Ir(N,N)(COD)BF$_4$ (according to Example 10)] (2 mol %), 2-ethylhexyl methacrylate (96 mol %) and 1.4-DVB (2 mol %)

107.3 mg (0.15 mmol) of the complex, prepared according to Example 10, 19.5 mg (0.15 mmol) of 1,4-DVB and 1.428 g (7.2 mmol) of 2-ethylhexyl methacry- After 19 hours at 60° C., the yield of 1-phenylbutanol is determined at 79.7% by gas chromatography (10% CW—20M, 185° C., isothermal).

To determine the enantiomer content according to Mosher, a sample (about 0.5 ml) is substantially freed from the solvent, and 50 μl of optically pure α-methoxy-α-trifluoromethylphenylacetyl chloride and 0.25 ml of dry pyridine are added at 0° C. After 15 minutes, the mixture is heated at 70° C. for 30 minutes and, after cooling, 3 ml of 10% citric acid solution are added, and the diastereomeric esters are extracted with diethyl ether.

An enantiomeric excess of (R)-1-phenylbutanol of ee=66.2% of (R) is determined by gas chromatography (capillary column CW 20, 190° C., isothermal).

Example 26:

5.5 ml of the solution obtained according to Example 14 are used for the catalytic enantioselective transfer hydrogenation of 1-phenylbutanone, similarly to Example 25. Under the reaction conditions for activation, the catalyst agglomerates to form a compact mass.

After 41 hours, the yield of 1-phenylbutanol is 12.4%, and the enantiomeric excess ee is 42.2% of (R).

Example 27:

0.8 ml of the emulsion obtained according to Example 15 is used for the catalytic, enantioselective transfer hydrogenation of 1-phenylbutanone, similarly to Example 25. However, the concentration ratio [S]/[cat.]=1000 is chosen. The heterogeneous catalyst is finely dispersed during the reaction.

After 6 hours, the yield of 1-phenylbutanol is 91.9%, and the enantiomeric excess ee=85.3% of (R).

Example 28:

70 ml of the emulsion obtained according to Example 15 are used for the catalytic, enantioselective transfer hydrogenation of 1-phenylbutanone, similarly to Example 25. The concentration ratio [S]/[cat.]=100 is chosen.

After 2 hours 50 minutes, the yield of 1-phenyl-butanol is 96.1%, and the enantiomeric excess ee=78.7% of (R).

Example 29:

The catalyst used according to Example 28 is recovered by separating it off from the supernatant solution, and the residual brown gel is washed twice with isopropanol in the absence of air. After decantation, the gel is dispersed with 30 ml of isopropanol, and 3.98 ml of 0.1 normal sodium hydroxide solution are added at 60° C. After 1 hour at 60° C., 1.48 g of 1-phenylbutanone and 30 ml of isopropanol are added. The procedure is continued as described in Example 25.

After 2 hours, the yield of 1-phenylbutanol is 94.5%, and the enantiomeric excess ee=82.6% of (R).

The processes of recovery, purification and reuse of the catalyst are repeated twice more.

The yields of 1-phenylbutanol are 94.6% after 3 hours 25 minutes and 90.9% after 3 hours 45 minutes, and the enantiomeric excesses are ee=80.8% of (R) and ee=78.8% of (R), respectively.

Example 30:

2.2 ml of the emulsion obtained according to Example 15 are used for the catalytic, enantioselective transfer hydrogenation of 1,4-diphenylbutanone similarly to Example 25.

After 6 hours 30 minutes, the yield of 1,4-diphenyl-butanol is 94.5%. The enantiomeric excess is determined, by the Mosher method, as ee=85.7% from the $^{19}$F-NMR spectrum of the diastereomeric esters.

Example 31:

7.0 ml of the emulsion obtained according to Example 17 are used for the catalytic, enantioselective transfer hydrogenation of 1-phenylbutanone, analogously to Example 25. The heterogeneous catalyst is coarsely dispersed during the reaction.

After 20 hours, the yield of 1-phenylbutanol is 85.8%, and the enantiomeric excess ee=78.7% of (S).

Example 32:

5 ml of the emulsion obtained according to Example 20 are used for the catalytic enantioselective transfer hydrogenation of 1-phenylbutanone, similarly to Example 25. The concentration ratio [S]/[cat.]=100 is chosen. After the end of the activation time, the reaction temperature is reduced to 24° C.

After 45 hours, the yield of 1-phenylbutanol is 95.2%, and the enantiomeric excess ee=90.6% of (R).

We claim:

1. An optically active compound of the formula I

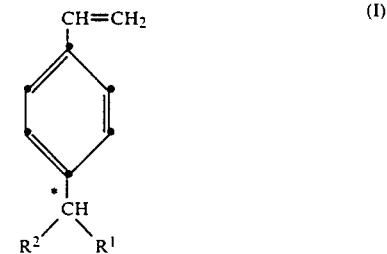

in which R$^1$ is C$_1$–C$_4$-alkyl, phenyl or benzyl, R$^2$ is a radical of the formula II or IIa

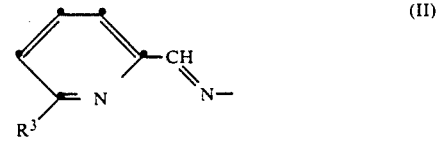

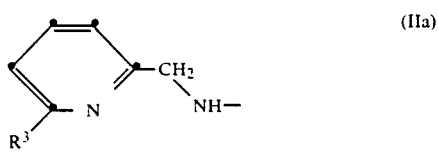

in which R$^3$ is H or —CH$_3$ and * represents predominantly R or predominantly S configuration.

2. A compound of the formula I according to claim 1, wherein R$^1$ is methyl or benzyl.

* * * * *